United States Patent [19]  [11]  4,304,782
Dumont et al.  [45]  Dec. 8, 1981

[54] PSYCHOTROPIC DEUTERATED DERIVATIVES OF PHENYLHYDANTOIN AND PHARMACEUTICAL COMPOSITIONS COMPRISING SUCH DERIVATIVES

[75] Inventors: Pierre A. Dumont, Gembloux; Jacques H. Poupaert, Ottignies, both of Belgium

[73] Assignee: Region Wallonne, Brussells, Belgium

[21] Appl. No.: 122,903

[22] Filed: Feb. 20, 1980

[30] Foreign Application Priority Data

Feb. 20, 1979 [FR] France ............................... 79 04209

[51] Int. Cl.$^3$ ........................................... A61K 31/415
[52] U.S. Cl. ................................. 424/273 R; 548/314
[58] Field of Search ..................... 424/273 R; 548/314

[56] References Cited

PUBLICATIONS

*Chemical Abstracts*, 88:105220s (1978) [Casey et al., *J. Labelled Compd. Radiopharm.* 1977, 13(4), 623–625].
Coombe, R. et al., *Aust. J. Chem.*, 1978, 31, 451–453.
*Chemical Abstracts*, 84:59303p (1976) [Kepler, J., *J. Labelled Compd.* 1975, 11(4), 601–603].
Casey, D. et al., *J. Labelled Compd. Radiopharm.* 1977, 13(4), 623–625.
Baty, J. et al., *Biomed. Mass Spec.*, 4(1), 36–41 (1977).

*Primary Examiner*—Richard A. Schwartz
*Attorney, Agent, or Firm*—Sughrue, Mion, Zinn, Macpeak and Seas

[57] ABSTRACT

Psychotropic composition comprising as an active constituent, a pharmaceutical composition, more particularly a psychotropic composition, characterized in that it comprises as an active constituent, a deuterated phenylhydantoin corresponding to the general formula

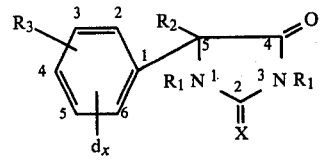

wherein radicals $R_1$ are identical or different and represent hydrogen or methyl, $R_2$ is ethyl or a substituted or unsubstituted phenyl group, which is deuterated or not, $R_3$ is hydrogen, halogen or a linear or ramified alkyl radical comprising 1 to 4 carbon atoms, a linear or ramified alkoxy radical comprising 1 to 4 carbon atoms, a trifluoromethyl, hydroxy, nitro or amino radical, X is an oxo, thio or methylene group and x is an integer of 1–5, one of its enantioners or one of its salts with a physiologically acceptable base, in combination with a pharmaceutically acceptable vehicle.

8 Claims, 1 Drawing Figure

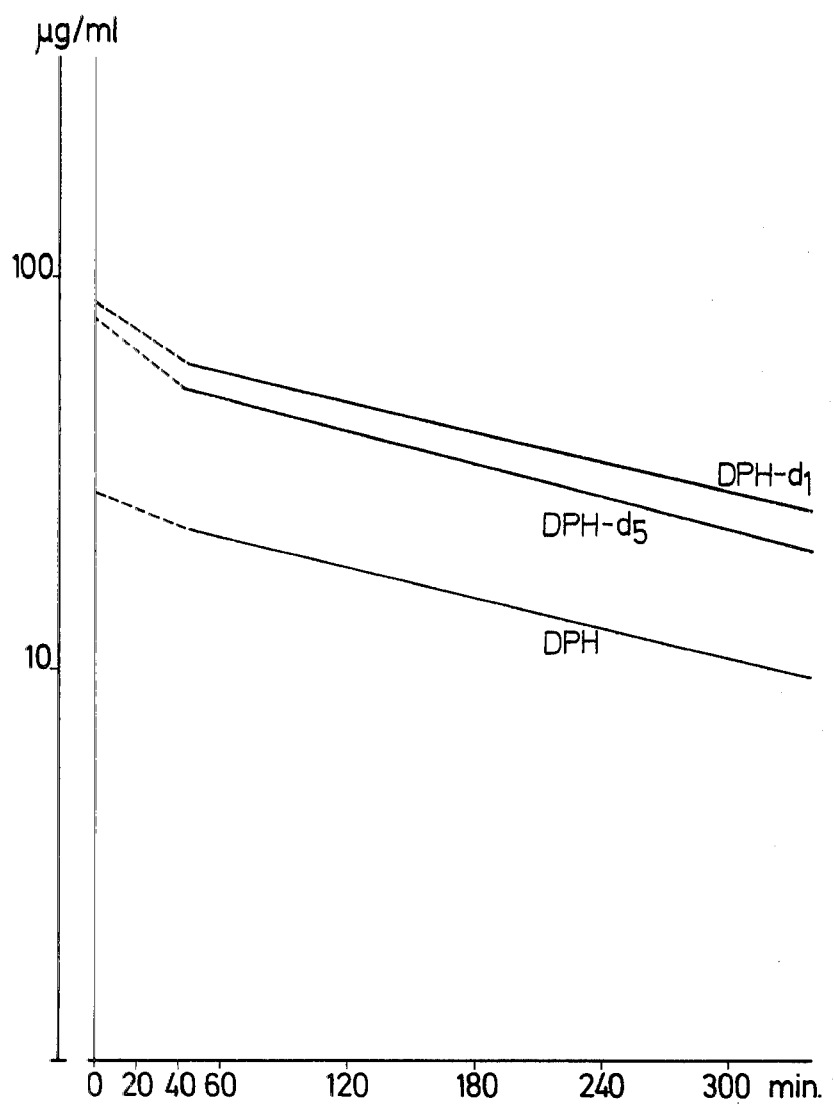

PSYCHOTROPIC DEUTERATED DERIVATIVES OF PHENYLHYDANTOIN AND PHARMACEUTICAL COMPOSITIONS COMPRISING SUCH DERIVATIVES

This invention relates to pharmaceutical compositions, more particularly to psychotropic compositions, comprising a phenylhydantoin derivative as active substance.

Pharmaceutical compositions having an antileptic action comprising 5,5-diphenylhydantoin as active substance are already known. It appears that 5,5-diphenylhydantoin has some drawbacks in respect to absorption, distribution, metabolism and excretion.

In order to study these phenomena on 5,5-diphenylhydantoin, it has already been proposed to label this substance with deuterium in order to carry out analyses. In this purpose, pentadeuterated and decadeuterated 5,5-diphenylhydantoin have already been prepared. These substances have, however, only been used for biochemical analysis.

This invention has for its purpose the provision of a psychotropic pharmaceutical composition which improves the anticonvulsive activity obtained with 5,5-diphenylhydantoin and which does not present the drawbacks of this latter substance.

It has been found that this problem can be solved according to the invention by means of a pharmaceutical composition comprising as active substance, a deuterated phenylhydantoin having the general formula:

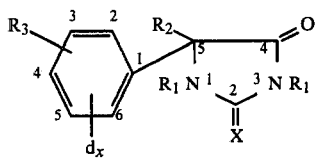

(I)

wherein radicals $R_1$ are identical or different and represent hydrogen or methyl, $R_2$ is ethyl or a substituted or unsubstituted phenyl group, which is deuterated or not, $R_3$ is hydrogen, halogen or a straight or branched chain alkyl radical comprising 1 to 4 carbon atoms, a straight or branched chain alkoxy radical comprising 1 to 4 carbon atoms, a trifluoromethyl, hydroxy, nitro or amino radical, X is an oxo, thio or methylene group and x is an integer of 1–5, one of its enantioners or one of its salts with a physiologically acceptable base, in combination with a pharmaceutically acceptable vehicle.

The accompanying FIGURE shows the evolution of active substance concentration with time as described in the Examples hereinafter.

According to an advantageous embodiment of the invention, the phenyldantoin is a deuterated diphenylhydantoin corresponding to the general formula:

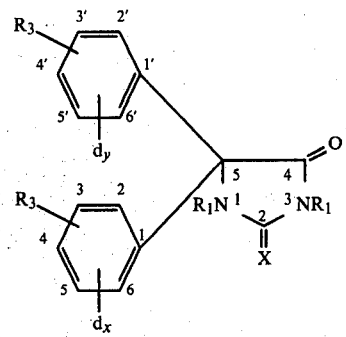

(II)

wherein radicals $R_3$ are identical or different and have the same meaning as previously, $R_1$ and X are such as hereinabove defined and $1 \leq x+y \leq 10$.

The formulae of enantiomers of compounds of formulae I and II are as follows:

and and

According to the invention, it has been found that (R,S)-5-phenyl-$d_5$-5-phenylhydantoin and enantioners thereof and 5,5-di-(phenyl-$d_5$)-hydantoin, which are known chemical substances, have as an effect the development of a higher anticonvulsive activity than diphenylhydantoin and accumulation in the cerebral tissue more favorably.

Moreover a new monodeuterated derivative of phenyldantoin has been provided, this chemical compound and its preparation process being consequently also an embodiment of the present invention. It is (R,S)-5-(paradeuterophenyl)-5-phenylhydantoin and enantiomers thereof.

The preparation of active substances according to the invention is described by more detail in the following examples which are, however, not limitative.

EXAMPLE 1

Process for preparing 5-(paradeuterophenyl)-5-phenylhydantoin (a) In a 500 ml steel bomb, 60 gr of 4-bromobenzophenone in 300 ml of dimethylformamide, 100 gr of solid ammonium carbonate and 30 gr of potassium cyanide in 100 ml of water are added. After closing the bomb, the reaction mixture is heated to 120° C. for 5 days, then poured under fast mechanical stirring into 2 l of water at 80° C., then acidified (concentrated HCl) and centrifuged after cooling in an ice-bath. A crude product is obtained, which is treated with 2 N sodium hydroxide (500 ml). The suspension is filtered; the filtrate is extracted three times with ether (total of 300 ml). The aqueous phase is acidified with concentrated hydrochloric acid to give 59 gr of 5-(parabromophenyl)-5-phenylhydantoin as a crude product. A recrystallization from ethanol gives 40 gr of pure product.

M.P.: 237°–239° C.

Thin layer chromatography: Rf 0,42(CHCl$_3$:acetone, 90:10, v/v).

IR: 1775, 1715 cm$^{-1}$ ($\nu_{c=o}$)(KBr)

(b) In a 500 ml hydrogenation bottle (Parr), 30 gr of 5-(parabromophenyl)-5-phenylhydantoin are added and dissolved in 250 ml of anhydrous dioxane and 30 ml of triethylamine 0.0.5 gr of 10% palladium on charcoal are added. The suspension is stirred for 24 hr. under an initial pressure of 0.34475 MPa of deuterium.

The catalyst and triethylamine hydrochloride are filtered out and the filtrate is evaporated to dryness under vacuum.

A recrystallization from ethanol gives 21 gr of the title product.

M.P.: 297°–298° C.

Thin layer chromatography: Rf 0.56 (CHCl$_3$:acetone, 90:10, v/v).

IR: 1775, 1740, 1720 cm$^{-1}$ ($\nu_{c=o}$) KBr.

Mass spectrum: 253 (m+), 224, 209, 181, 166, 105, 104, 78, 77.

Elemental analysis, %:

|  | N | C | H |
|---|---|---|---|
| Calculated: | 11.06 | 71.12 | 5.17 |
| Found: | 10.89 | 71.41 | 4.93 |

EXAMPLE 2

Process for preparing 5-(paradeuterophenyl)-5-phenylhydantoin (a) In a 250 flask equipped with a condenser, 3 gr of parachlorobenzil and 80 ml of ethanol (95%) are added. The product is dissolved by reflux heating for 5 minutes. Then 1.5 gr of urea and 1.2 gr of solid KOH are added and also 20 additional ml of ethanol.

A white precipitate immediately appears. After heating at reflux for 8 hr., the reaction mixture is then poured into 400 ml of water and filtered, and the filtrate is acidified (concentrated HCl). The obtained 5-(parachlorophenyl)-5-phenylhydantoin is centrifuged. It is dried under vacuum (80° C./30 mm of Hg) and recrystallized from ethanol: water (80:20, v/v). Yield: 0.85 gr.

M.P.: 243°–244° C. (according to prior art: 243° C.).

Thin layer chromatography: Rf 0.45 (CHCl$_3$:acetone, 90:10, v/v).

(b) One proceeds in a similar manner as in Example 1b.

EXAMPLE 3

Process for preparing 5-phenyl-d$_5$-5-phenylhydantoin (a) In a three-necked flask provided with a dropping funnel, a mechanical stirrer and a condenser with a calcium chloride tube, 100 ml of benzene -d$_6$, 60 gr of anhydrous aluminium trichloride and 200 ml of carbon disulfide are added. This mixture is cooled in a ice-bath for 15 minutes under mechanical stirring. Over 20 minutes, 55 ml of benzoyl chloride diluted in 100 ml of carbon disulfide are then dropwise added under fast stirring. The reaction mixture is then maintained for 30 minutes in the ice-bath after the addition is complete, then refluxed for 6 hours. The reaction mixture is decomposed on 2 kg of ice, extracted with dichloromethane and evaporated to dryness. The residue is taken up in 300 ml of benzene and treated with 300 ml of 2 N NaOH. The phases are separated and the aqueous phase is extracted with 2×150 ml of benzene. The organic phase is dried (MgSO$_4$) and concentrated under vacuum. A distillation under vacuum is then provided, which gives 71 gr of benzophenone-d$_5$. B.P. (400 mm of Hg): 190°–195° C.

(b) In a 500 ml steel bomb, 60 gr of benzophenone-d$_5$, 300 ml of dimethylformamide, 30 gr of potassium cyanide dissolved in 100 ml of water and 100 gr of ammonium carbonate are successively added. The reaction mixture is heated for 5 hours at 120° C. in a thermostat-controlled oil bath.

Isolation of the title product is carried out as previously for 5-(parabromophenyl)-5-phenylhydantoin. The yield of crude product is 58.5 gr. The production of product recrystallized from ethanol is 44 gr.

B.P.: 297°–298° C.

Thin layer chromatography: Rf 0.56 (CHCl$_3$:acetone, 90:10, v/v).

IR: 1775, 1740, 1720 cm$^{-1}$ ($\nu_{c=o}$) KBr.

Mass spectrum: 257 (m+), 228, 214, 184, 170, 109, 104, 82, 77.

Elemental analysis, %:

|  | N | C |
|---|---|---|
| Calculated: | 10.86 | 69.85 |
| Found: | 10.72 | 70.29 |

EXAMPLE 4

Process for preparing 5,5-di-(phenyl-d$_5$)-hydantoin (a)

In a 500 ml three-necked flask provided with a condenser with a calcium chloride tube, a mechanical stirrer and a dropping funnel, 45 gr of aluminum chloride and 100 ml of anhydrous carbon tetrachloride are added. The mixture is cooled in a ice-bath under stirring. A mixture of 55 ml of benzene-d$_6$ and 55 ml of carbon tetrachloride is then dropwise added. After the addition is complete (1 hour), the ice-bath is removed and stirring is continued for 6 hours. The mixture is then allowed to cool for 24 hours. 200 ml of 2 N hydrochloric acid are slowly added under stirring. The carbon tetrachloride is extracted with $3 \times 150$ ml of benzene. After drying ($MgSO_4$) the product is concentrated under vacuum.

A distillation under vacuum gives 40 gr of benzophenone-$d_{10}$.

B.P. (12 mm of Hg): 180°–185° C.

(b) The operating step is identical to that of Example 3b.

Production: 40 gr.

B.P.: 295°–298° C.

Thin layer chromatography: Rf 0.56 ($CHCl_3$:acetone, 90:10, v/v).

IR: 1775, 1740, 1720 ($\nu c=o$) KBr.

Mass spectrum : 262, 232, 220, 189, 152, 109, 82.

Elemental analysis, %:

|  | N | C |
|---|---|---|
| Calculated: | 10.68 | 68.89 |
| Found: | 10.51 | 68.77 |

The compositions according to the invention can be used as psychotropic products, in particular as anticonvulsive products, and can be thus in particular administered in the treatment of epilepsy.

These compositions can be administered as tablets, wafers, gelatin capsules, capsules, coated pills or as solutions. they can be for example administered as gelatin capsules containing as a unit dosage 30 to 200 mgr of active substance as a powder, the daily dose being 1.5 to 5 mgr/kg of body weight. The compositions according to the invention can also be administered for example intraperitoneally, as a solution, or intravenously, as a unit dose of 100 to 200 mg of active substance in solution.

The active substances according to the invention were tested in order to examine their activity and their effects in comparison with known diphenylhydantoin (DPH). In these tests as follows, 5-(paradeuterophenyl)-5-phenylhydantoin will be designated by DPH-$d_1$ and 5-phenyl-$d_5$-5-phenylhydantoin by DPH-$d_5$.

To examine the anticonvulsive activity of these substances, they were subjected to testing as to protection against convulsions caused by pentylene tetrazole on adult female rat (Wistar strain: 200–220 gr). One, two or four hours after oral administration of hydantoins (100 and 200 mgr/kg: solution in dimethyl sulfoxide/propylene glycol), animals have received a dose of 100 mgr/kg of pentylene tetrazole (PTZ) intraperitonally, then they were maintained under observation for 1 hour. The absence of appearance of convulsions was considered as a positive response. The results are expressed in the following table I as the ratio between the number of protected animals and the total number of animals.

TABLE I

| Protection of rats against the convulsive effect of PTZ | | | |
|---|---|---|---|
|  | DPH | DPH-$d_1$ | DPH-$d_5$ |
| A. Doses of active substances at fixed time (1 hour) | | | |
| 100 mgr/kg | 4/25 | 9/14 | 7/20 |
| 200 mgr/kg | 5/35 | 11/30 | 11/35 |
| B. Time with fixed dose (100 mgr/kg). | | | |

TABLE I-continued

| Protection of rats against the convulsive effect of PTZ | | | |
|---|---|---|---|
|  | DPH | DPH-$d_1$ | DPH-$d_5$ |
| 1 hour | 4/25 | 9/14 | 7/20 |
| 2 hours | 2/10 | 4/10 | 2/10 |
| 4 hours | 0/10 | 2/10 | 0/10 |

The analysis of these results (Table II) was made by a non-parametral method (tables of frequence $2 \times 2$: $X^2$ differences). The research of significant differences has been made on the following aspects: between DPH and deuterated DPH at 1 hour at doses of 100 and 200 mgr/kg, between DPH and deuterated DPH at any time and at a dose of 100 mgr/kg, between doses of 100 and 200 mgr/kg and between the times.

TABLE II

| Statistical analysis Non-parametral method, Tables of frequence $2 \times 2$; $\chi^2$ differences | | | |
|---|---|---|---|
|  | DPH | DPH-$d_1$ | DPH-$d_5$ |
| 1. Between DPH and deuterated DPH (at 1 hour) | | | |
| 100 mgr/kg |  | 9.42** | 2.17 |
| 200 mgr/kg |  | 4.36* | 2.92 |
| 2. Between DPH and deuterated DPH at any time | | | |
| 100 mgr/kg |  | 9.40** | 1.22 |
| 3. Between the doses (100 and 200 mgr/kg) | NS | NS | NS |
| 4. Between the times | | | |
| 1 hour | NS | 3.93* | 3.58 |
| 2 hours + 4 hours | | | |

*$P < 0.05$
**$P < 0.01$
NS: not significant.

The statistical analysis clearly indicates that DPH-$d_1$ better protects the animals against the convulsive effect of PTZ than DPH, the differences are highly significant at 100 mgr/kg (9.42**) and significant at 200 mgr/kg (4.36*). This effect is retained for 4 hours (9.40**) but is more marked at the first hour (3.93*). A difference in the same direction, close to the significance limit, has also been observed with DPH-$d_5$.

Determinations of blood levels were made on rats and mice of either sex after administration of substances to be tested intravenously and to this hand the measure of radioactivity of products labelled with $^{14}C$ was used as titration method.

After intravenous injection of a dose of 50 mgr/kg of the substance to be examined (alkaline solution) to 5 female rats, the evolution of substance concentration ($\mu$g/ml) in the blood versus time was examined by using the method of labelling with $^{14}C$ (as shown in the FIGURE).

If attention is paid to the comparative behaviour of DPH, on the one hand, and deuterated analogues thereof, on the other hand, distinct differences appear in the various experiments made.

The contents of the various tissues in DPH, DPH-$d_1$ and DPH-$d_5$ have been determined at two times after oral administration (male mice, female rats, titration by gaseous chromatography).

The whole results are mentioned in the following table III. The indicated values represent the ratio of active substance concentrations in the brain and blood.

After oral administration, these values as well in rat as in mouse show a trend, which is marked to very marked, to be higher for deuterated DPH than for DPH itself. The deuteration would thus modify the brain/blood repartition towards the brain, a phenomenon which would be in relation with the higher anticonvulsive activity of the DPH-$d_1$ and DPH-$d_5$.

TABLE III

Repartition in tissues
Oral administration
Titration by gaseous chromatography

| | Mice: 20–25gr, ♂ 100 mgr/kg | | | |
|---|---|---|---|---|
| | After 2 hours | | After 24 hours | |
| | DPH | DPH-$d_5$ | DPH | DPH-$d_5$ |
| Ratio brain/blood | 1.45 ± 0.10 | 2.35 ± 0.26 | 2.09 ± 0.22 | 2.97 ± 0.30 |
| | Rat: ± 200 gr ♀ 100 mg/kg | | | |
| After 1 hour | DPH | DPH-$d_5$ | DPH-$d_1$ | |
| Ratio brain/blood | 0.90 ± 0.13 | 2.15 ± 0.37 | 2.10 ± 0.41 | |
| After 2 hours | DPH | DPH-$d_5$ | DPH-$d_1$ | |
| Ratio brain/blood | 5.91 ± 0.93 | 4.49 ± 1.33 | 15.5 ± 3.7 | |

It clearly appears from all these tests that deuteration of diphenylhydantoin improves the anticonvulsive activity of the product, modifies its blood parmacokinetics and promotes accumulation of the product in the cerebral tissue.

It is to be understood that this invention is in no way limited to the embodiments such as hereinabove described and that many modifications can be made therein without departing from the scope of this invention.

We claim:

1. A psychotropic pharmaceutical composition, which comprises as an active constituent, a therapeutically effective amount of a deuterated phenylhydantoin corresponding to the formula

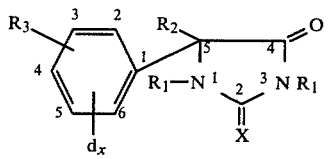

(I)

wherein $R_1$, which may be the same or different, represents hydrogen or methyl, $R_2$ is ethyl, unsubstituted phenyl or phenyl substituted by halogen, straight chain or branched chain alkyl comprising 1 to 4 carbon atoms, straight or branched chain alkoxy comprising 1 to 4 carbon atoms, trifluoromethyl, nitro or amino, which phenyl or substituted phenyl may be deuterated, $R_3$ is hydrogen, halogen, straight chain or branched chain alkyl comprising 1 to 4 carbon atoms, straight or branched chain alkoxy comprising 1 to 4 carbon atoms, trifluoromethyl, nitro or amino, X is oxo, thio or methylene and x is an integer, with the proviso that the deuteration in $R_2$ and due to $d_x$ is such that said deuterated phenylhydantoin corresponding to the formula (I) is a mono- or penta-deuterated phenylhydantoin, one of its enantiomers or one of its salts with a physiologically acceptable base, in combination with a pharmaceutically acceptable vehicle.

2. A composition according to claim 1, wherein the phenylhydantoin is a deuterated diphenylhydantoin of the formula:

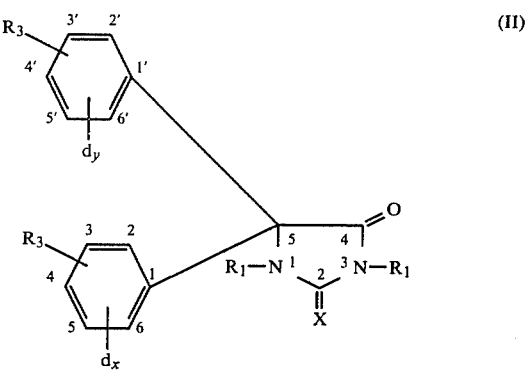

(II)

wherein $R_3$, which may be the same or different has the same meaning as defined in claim 1, $R_1$ and X are as defined in claim 1 and $x+y=1$ or 5.

3. A composition according to either of claims 1 or 2, wherein, in formulae I or II, said halogen for $R_3$ is chlorine, fluorine, bromine or iodine.

4. A composition according to claim 2, wherein said deuterated diphenylhydantoin is selected from the group consisting of (R,S)-5-(paradeuterophenyl)-5-phenylhydantoin, (R)-5-(paradeuterophenyl)-5-phenylhydantoin and (S)-5-(paradeuterophenyl)-5-phenylhydantoin.

5. A composition according to claim 2, wherein said deuterated diphenylhydantoin is selected from the group consisting of (R,S)-5-phenyl-$d_5$-5-phenylhydantoin, (R)-5-phenyl-$d_5$-5-phenylhydantoin and (S)-5-phenyl-$d_5$-5-phenylhydantoin.

6. A composition according to claim 1, in the form of a unit dosage.

7. A composition according to claim 6, in the form of a tablet, wafer, capsule, coated pill or solution.

8. A method for treating epilepsy, comprising administering a psychotropic composition according to claim 1 to humans or animals in need of such treatment.

* * * * *